(12) United States Patent
Zhuang et al.

(10) Patent No.: US 11,779,668 B2
(45) Date of Patent: Oct. 10, 2023

(54) UVC-INTEGRATED LED STRUCTURE ADAPTED TO AIR STERILIZATION-AND-DISINFECTION GRILLES

(71) Applicant: SHENZHEN YITOA INTELLIGENT INDUSTRIAL CO., LTD, Shenzhen (CN)

(72) Inventors: Junhuang Zhuang, Shenzhen (CN); Zhihong Zheng, Shenzhen (CN)

(73) Assignee: SHENZHEN YITOA INTELLIGENT INDUSTRIAL CO., LTD, Shenzhen (CN)

( * ) Notice: Subject to any disclaimer, the term of this patent is extended or adjusted under 35 U.S.C. 154(b) by 32 days.

(21) Appl. No.: 17/717,046

(22) Filed: Apr. 9, 2022

(65) Prior Publication Data
US 2023/0233718 A1 Jul. 27, 2023

(30) Foreign Application Priority Data
Jan. 25, 2022 (CN) .......................... 202220209906.4

(51) Int. Cl.
| | | |
|---|---|---|
| *A61L 2/10* | (2006.01) | |
| *F21V 33/00* | (2006.01) | |
| *F24F 8/22* | (2021.01) | |
| *F21Y 115/10* | (2016.01) | |

(52) U.S. Cl.
CPC ............ *A61L 2/10* (2013.01); *F21V 33/0064* (2013.01); *F24F 8/22* (2021.01); *F21Y 2115/10* (2016.08)

(58) Field of Classification Search
CPC ...... A61L 2/10; A61L 2/08; F24F 8/22; F24F 13/082; F24F 13/08; F24F 8/20; F21V 33/0064; F21V 33/0088; F21V 33/0092; F21V 99/00; F21Y 2115/10; F16S 3/00; E06B 9/01; E06B 9/02; E06B 7/08
See application file for complete search history.

(56) References Cited

U.S. PATENT DOCUMENTS

| | | | | |
|---|---|---|---|---|
| 3,996,845 | A * | 12/1976 | Harris ...................... | F24F 13/08 454/320 |
| 10,072,869 | B2 * | 9/2018 | Zakula .................. | F24F 13/078 |
| 2006/0080890 | A1 * | 4/2006 | Nowak .................. | F24F 13/082 44/560 |
| 2017/0219243 | A1 * | 8/2017 | Yi ............................ | F24F 11/30 |

\* cited by examiner

*Primary Examiner* — Bao Q Truong
(74) *Attorney, Agent, or Firm* — Li & Cai Intellectual Property (USA) Office

(57) ABSTRACT

A UVC-integrated LED structure adapted to air sterilization-and-disinfection grilles is provided. The UVC-integrated LED structure includes a housing, an opening disposed at top of the housing, multiple wavy grilles engaged with both sides of inner wall of the opening, placement grooves openly disposed at one side of the wavy grilles, and COB light boards disposed inside the placement grooves. The UVC-integrated LED structure installs the COB light boards at the placement grooves. The structure allows the COB light boards to be hidden on the surfaces of the wavy grilles for decreasing height of the COBs. Therefore, air resistance can be reduced when the ultraviolet ray irradiates on the passing air. The impact of dust being adhered to the COB light boards can be reduced. The air passing through the multiple wavy grilles can be sterilized and disinfected.

6 Claims, 3 Drawing Sheets

UVC-INTEGRATED LED STRUCTURE ADAPTED TO AIR STERILIZATION-AND-DISINFECTION GRILLES

CROSS-REFERENCE TO RELATED PATENT APPLICATION

This application claims the benefit of priority to Patent Application No. 202220209906.4, filed on Jan. 25, 2022 in People's Republic of China. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure is related to a technical filed of air sterilization and disinfection, and more particularly to a UVC-integrated LED structure that is equipped with grilles used for air sterilization and disinfection.

BACKGROUND OF THE DISCLOSURE

An air purifier, which is also known as an air cleaner, an air purifier or a purifier, indicates a product that is able to absorb, decompose or transform various air pollutants can effectively improve air cleanliness. The air purifier includes different technologies and mediators that are used to provide clean and safe air for users. The general technologies used in the air purifier are such as technologies relating to adsorption, negative and positive ions, catalysis, photocatalyst, superstructured light mineralization, HEPA high-efficiency filtration, and/or electrostatic dust precipitation.

A UVC (ultraviolet ray in "C" spectrum) integrated LED module is one of the important and requisite components in the air purifier. The UVC-integrated LED module includes a PCB substrate, multiple wavy grilles and a COB (chip on board) light board. However, in the conventional technology, general COB light boards are engaged with troughs of the wavy grilles and resulting in bumped areas. When air passes between the wavy grilles, the dust may be accumulated on the COB light boards easily and the accumulated dust may affect energy output of ultraviolet ray.

SUMMARY OF THE DISCLOSURE

The present disclosure provides a UVC-integrated LED structure that can be used for air sterilization-and-disinfection grilles that is used for solving drawbacks existed in the background arts. In an aspect of the present disclosure, COB light boards are disposed inside placement grooves that are openly disposed on troughs of the wavy grilles. The COB light boards can therefore be hidden on the surfaces of the wavy grilles as much as possible. Therefore, the height of COB can be decreased. The structure can reduce air resistance when the ultraviolet ray irradiates on the passing air. Further, impact of dust being adhered to the COB light boards on energy output of the ultraviolet ray can be reduced.

For implementing the above technical purpose, a UVC-integrated LED structure adapted to air sterilization-and-disinfection grilles is provided. The UVC-integrated LED structure includes a housing, an opening openly disposed on a top of the housing, multiple wavy grilles engaged with two sides of inner wall of the opening, placement grooves openly disposed on one side of the wavy grilles, and multiple COB light boards disposed inside the placement grooves.

Further, the wavy grille can be in a tile shape.

Still further, a grille passage is openly disposed between every two adjacent wavy grilles.

Further, a plurality of grille passages are separated by the multiple wavy grilles and the multiple wavy grilles are arranged uniformly.

Still further, the both sides of inner wall of the opening are mounted with a PCB substrate, and the two ends of the COB light boards are engaged to the PCB substrate respectively.

Further, multiple lamp beads are disposed on one side of the COB light board.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
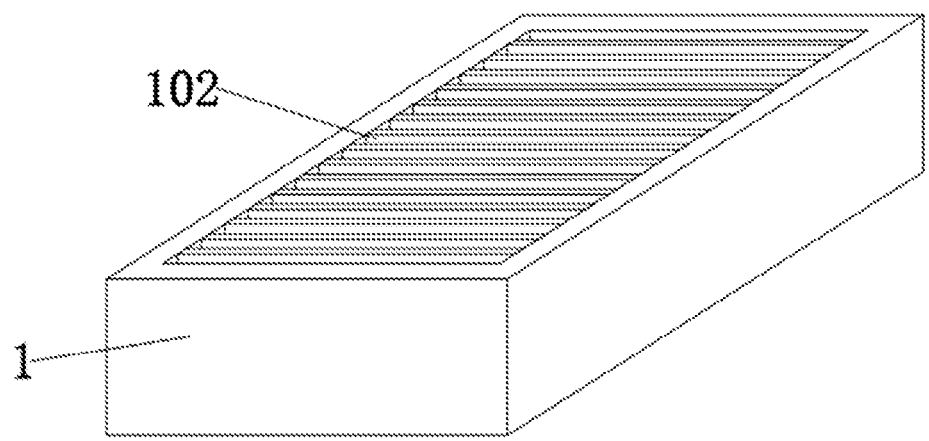
FIG. 1 is a schematic diagram depicting an overall structure of a UVC-integrated LED structure according to one embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

The UVC-integrated LED structure that is adapted to air sterilization-and-disinfection grilles. The UVC-integrated LED structure provides following beneficial effects.

The structure of the present disclosure provides following beneficial effects. COB light boards are mounted on placement grooves that are openly disposed on the troughs of wavy grilles. The structure allows the COB light boards to be hidden on the surfaces of the wavy grilles as much as possible. Since the height of COB can be decreased, the air resistance can be reduced when the ultraviolet ray irradiates on the passing air. The impact of dust being adhered to the COB light boards on energy output of the ultraviolet ray can be reduced.

Therefore, the air passing through the multiple wavy grilles can be sterilized and disinfected since the multiple wavy grilles are disposed at the opening of the housing.

Embodiments

Figure 2:
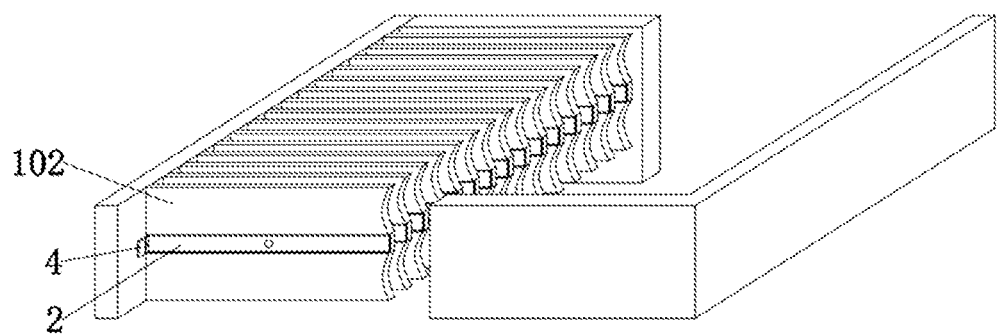
FIG. 2 is an exploded view of an overall structure of the UVC-integrated LED structure in one embodiment of the present disclosure.
Figure 3:
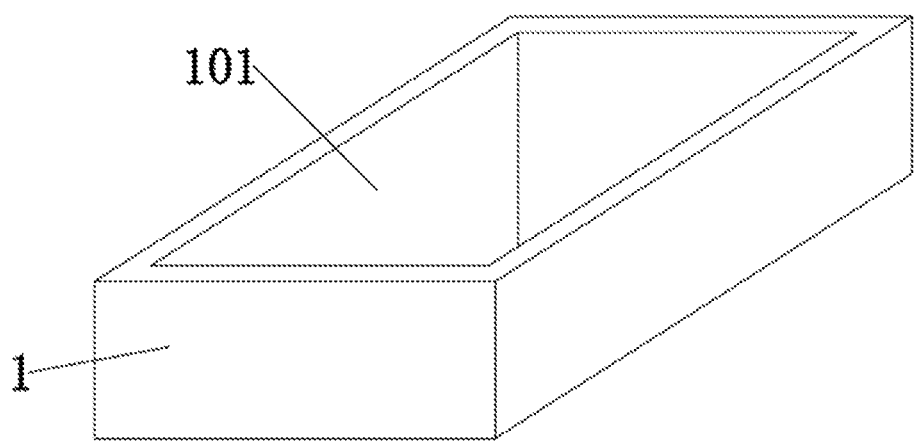
FIG. 3 is a schematic diagram depicting a housing of the UVC-integrated LED structure in one embodiment of the present disclosure.
Figure 4:
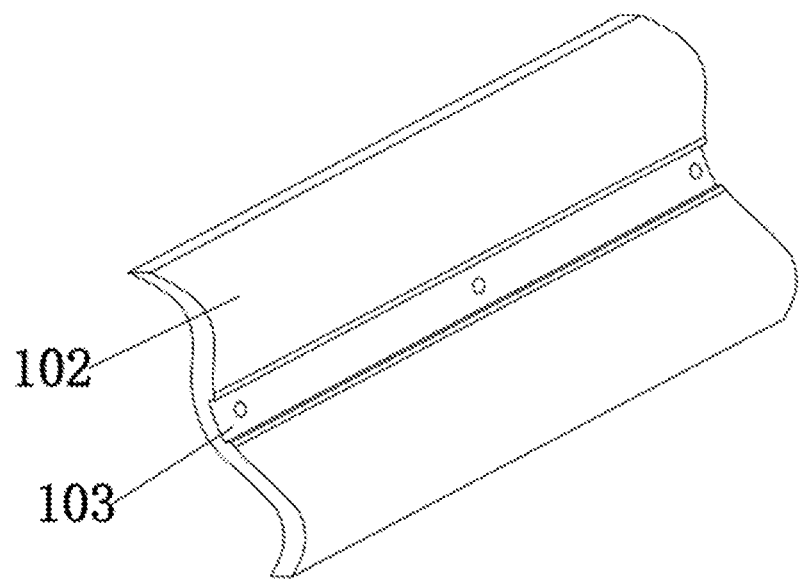
FIG. 4 is a schematic diagram depicting wavy grille structure in one embodiment of the present disclosure.
Figure 5:
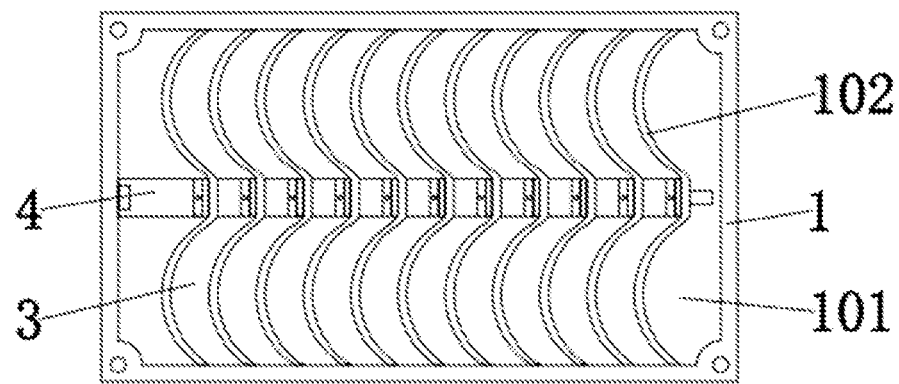
FIG. 5 is a schematic diagram depicting a top view of the housing of the UVC-integrated LED structure according to one embodiment of the present disclosure.
Figure 6:
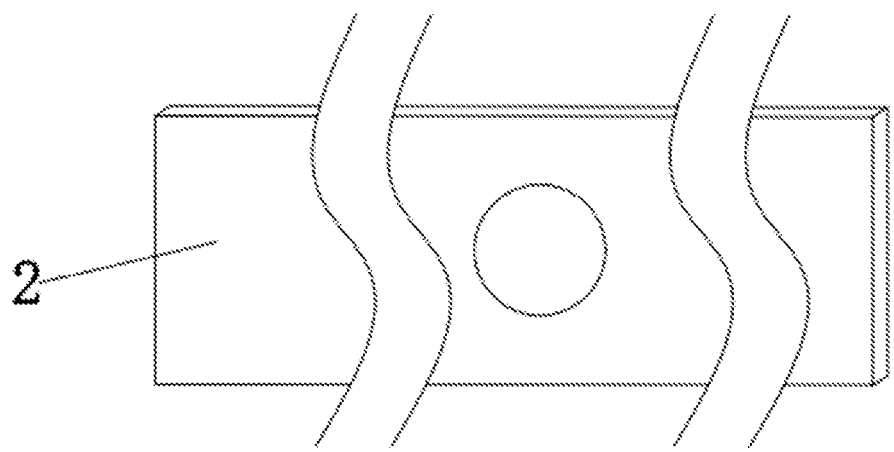
FIG. 6 is a schematic diagram depicting a COB light board according to one embodiment of the present disclosure.

References are made to FIGS. 1 to 6. A UVC-integrated LED structure that is adapted to air sterilization-and-disinfection grilles is provided. The UVC-integrated LED structure includes a housing 1, multiple wavy grilles 102 that are openly disposed on an opening 101 at the top of the housing 1, and the wavy grilles 102 engaged with both sides of inner wall of the opening 101 form multiple grille passages 3. The grille passages 3 allow the UVC-integrated LED structure to irradiate ultraviolet ray for air sterilization. A COB light board 2 can be mounted on placement grooves 103 that are openly disposed at one side of the wavy grilles 102. The COB light boards 2 disposed inside the placement grooves 103 irradiate ultraviolet ray for air disinfection.

Further, the wavy grille 102 can be in a tile shape that can be disposed in the placement groove 103 through the COB light board 2. Therefore, the COB light boards 2 disposed at troughs of the wavy grilles 102 can be hidden on the surface of the wavy grilles 102 as much as possible. Further, the height of the COB light boards 2 disposed inside the placement grooves 103 can be effectively reduced. The COB light boards 103 form parts of the surfaces of the wavy grilles 102, and air resistance can be reduced when the ultraviolet ray irradiates on the passing air. Since the air resistance is small, the impact of dust being adhered to the COB light boards 2 on energy output of the ultraviolet ray can be reduced. The output of the ultraviolet ray can therefore be guaranteed.

Further, a grille passage 3 is openly disposed between two adjacent wavy grilles 102. When a device having the UVC-integrated LED structure is in operation, the air can pass through the grille passage 3.

Further, the plurality of grille passages 3 are separated by the multiple wavy grilles 102, and the multiple wavy grilles 102 are arranged uniformly. The grille passages 3 with a uniform diameter allow the air flow passing the grille passages 3 to be consistent. The effect of air disinfection and sterilization can be guaranteed.

Still further, both sides of inner wall of the opening 101 are mounted with the PCB substrate 4, and the two ends of the COB light boards 2 are engaged with the PCB substrate 4. The PCB substrate 4 can supply power to the COB light boards 103 when the device is in operation.

Further, there are multiple lamp beads disposed on one side of the COB light board 2. When the COB light board 2 is in use, the lamp beads irradiate ultraviolet rays and the air passing the grille passages 3 can be disinfected and sterilized.

In the embodiments, the description with respect to each of the embodiments has its own emphasis, and parts of some of the embodiments that lack details can refer to the descriptions of other embodiments.

In conclusion, the above embodiments provide detailed descriptions relating to the UVC-integrated LED structure that is able to conduct air sterilization and disinfection. Through the UVC-integrated LED structure, the air passing through the multiple wavy grilles can be sterilized and disinfected.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A UVC-integrated LED structure, which is adapted to air sterilization-and-disinfection grilles, comprising:
   a housing;
   an opening at a top of the housing;
   multiple wavy grilles engaged with both sides of an inner wall of the opening;
   at least one placement grooves openly disposed at one side of the multiple wavy grilles; and
   multiple COB light boards disposed inside the placement grooves.

2. The UVC-integrated LED structure according to claim 1, wherein the wavy grille is in a tile shape.

3. The UVC-integrated LED structure according to claim 1, wherein, a grille passage is openly disposed between every two adjacent wavy grilles.

4. The UVC-integrated LED structure according to claim 1, wherein the UVC-integrated LED structure includes a plurality of grille passages which are separated by the multiple wavy grilles and the multiple wavy grilles are arranged uniformly.

5. The UVC-integrated LED structure according to claim 1, wherein both sides of inner wall of the opening are disposed with a PCB substrate, and two ends of the COB light boards are engaged with the PCB substrate respectively.

6. The UVC-integrated LED structure according to claim 1, wherein multiple lamp beads are disposed on one side of the COB light board.

* * * * *